(12) United States Patent
Cottrell

(10) Patent No.: US 6,960,436 B2
(45) Date of Patent: Nov. 1, 2005

(54) QUANTITATIVE METHYLATION DETECTION IN DNA SAMPLES

(75) Inventor: Susan Cottrell, Seattle, WA (US)

(73) Assignee: Epigenomics AG, Berlin (DE)

( * ) Notice: Subject to any disclaimer, the term of this patent is extended or adjusted under 35 U.S.C. 154(b) by 0 days.

(21) Appl. No.: 10/068,553

(22) Filed: Feb. 6, 2002

(65) Prior Publication Data

US 2003/0148290 A1 Aug. 7, 2003

(51) Int. Cl.$^7$ .......................... C12Q 1/68; C07H 21/02; C07H 21/04
(52) U.S. Cl. .......................... 435/6; 536/23.1; 536/24.3
(58) Field of Search .............................. 435/6; 536/23.1, 536/24.3

(56) References Cited

U.S. PATENT DOCUMENTS

| | | | |
|---|---|---|---|
| 6,331,393 B1 * | 12/2001 | Laird et al. | |
| 2003/0017465 A1 * | 1/2003 | Kay | |
| 2003/0082600 A1 * | 5/2003 | Olek et al. | |
| 2003/0087258 A1 * | 5/2003 | Shuber | |

OTHER PUBLICATIONS

Cottrell et al., Annals of the New York Academy of Sciences 983 :120–130 (2003).*
Eads et al., Nucleic Acids Research 28(8) E32 : i–viii (2000).*
Herman et al., PNAS 93 : 9821–9826 (1996).*
Gonzalgo et al., Nucleic Acids Research 25 (12) : 2529–2531 (1997).*
The Stratagene Catalog, p. 39 (1988).*

* cited by examiner

*Primary Examiner*—Ethan Whisenant
(74) *Attorney, Agent, or Firm*—Kriegsman & Kriegsman

(57) ABSTRACT

Described is a method for methylation detection in a DNA sample. An isolated genomic DNA sample is treated in a manner capable of distinguishing methylated from unmethylated cytosine bases. The pretreated DNA is amplified using at least one oligonucleotide primer, a polymerase and a set of nucleotides of which at least one is labeled with a first type of label. A sequence-specific oligonucleotide probe, marked with a second type of label, hybridizes to the amplification product and a FRET reaction occurs if a labeled oligonucleotide is present in close proximity in the amplification product. The method determines the level of methylation of a sample by measuring the extent of fluorescence resonance energy transfer (FRET) between the donor and acceptor fluorophore.

24 Claims, 3 Drawing Sheets

QUANTITATIVE METHYLATION DETECTION IN DNA SAMPLES

FIELD OF THE INVENTION

This invention relates to the analysis of nucleic acids, especially to the analysis of methylation patterns in genomic DNA by providing a means of detecting nucleotides, that are characteristic for methylated sites after bisulfite treatment of the genomic DNA. The method utilises the incorporation of labels and the detection of fluorescence resonance energy transfer (FRET) of the amplified sample DNA.

PRIOR ART

DNA Methylation

The levels of observation that have been studied in recent years in molecular biology have concentrated on genes, the translation of those genes into RNA, and the transcription of the RNA into protein. There has been a more limited analysis of the regulatory mechanisms associated with gene control. Gene regulation, for example, at what stage of development of the individual a gene is activated or inhibited, and the tissue specific nature of this regulation is less understood. However, it can be correlated with a high degree of probability to the extent and nature of methylation of the gene or genome. From this observation it is reasonable to infer that pathogenic genetic disorders may be detected from irregular genetic methylation patterns.

The efforts of the Human Genome project are concentrated on the sequencing of the human genome. It is expected that this will yield considerable therapeutic and diagnostic benefits for the treatment of disease.

However, these efforts have so far been unable to address a significant aspect of genetic disorders, the epigenetic factor. The epigenetic regulation of gene transcription has been shown to effect many disorders. One of the most significant epigenetic mechanisms so far identified has been the methylation of cytosine. The methylation of cytosine at the 5 position is the only known modification of genomic DNA. Although the exact mechanisms by which DNA methylation effects DNA transcription are unknown, the relationship between disease and methylation has been well documented. In particular methylation patterns of CpG islands within regulatory regions of genome appear to be highly tissue specific. Therefore, it follows that misregulation of genes may be predicted by comparing their methylation pattern with phenotypically 'normal' expression patterns. The following are cases of disease associated with modified methylation patterns.

Head and neck cancer (Sanchez-Cespedes M et al. "Gene promoter hypermethylation in tumors and serum of head and neck cancer patients" Cancer Res. 2000 February 15;60 (4):892–5)

Hodgkin's disease (Garcia J F et al "Loss of p16 protein expression associated with methylation of the p16INK4A gene is a frequant finding in Hodgkin's disease" Lab invest 1999 December; 79 (12):1453–9)

Gastric cancer (Yanagisawa Y et al. "Methylation of the hMLH1 promoter in familial gastric cancer with microsatellite instability" Int J Cancer 2000 January 1; 85 (1):50–3)

Prader-Willi/Angelman's syndrome (Zeschnigh et al "Imprinted segments in the human genome: different DNA methylation patterns in the Prader Willi/Angelman syndrome region as determined by the genomic sequencing method" Human Mol. Genetics (1997) (6) 3 pp 387–395)

ICF syndrome (Tuck-Muller et al "CMDNA hypomethylation and unusual chromosome instability in cell lines from ICF syndrome patients" Cytogenet Call Genet 2000; 89(1–2):121–8

Dermatofibroma (Chen T C et al "Dermatofibroma is a clonal proliferative disease" J Cutan Pathol 2000 January; 27 (1):36–9)

Hypertension (Lee S D et al. "Monoclonal endothelial cell proliferation is present in primary but not secondary pulmonary hypertension" J clin Invest 1998 Mar. 1, 101 (5):927–34)

Autism (Klauck S M et al. "Molecular genetic analysis of the FMR-1 gene in a large collection of autistic patients" Human Genet 1997 August; 100 (2): 224–9)

Fragile X Syndrome (Hornstra I K et al. "High resolution methylation analysis of the FMR1 gene trinucleotide repeat region in fragile X syndrome" Hum Mol Genet 1993 October, 2(10):1659–65)

Huntigton's disease (Ferluga J et al. "possible organ and age related epigenetic factors in Huntington's disease and colorectal carcinoma" Med hyptheses 1989 May; 29(1);51–4

All of the above documents are hereby incorporated by reference.

Bisulphite Treatment

A relatively new and currently the most frequently used method for analyzing DNA for 5-methylcytosine is based upon the specific reaction of bisulfite with cytosine which, upon subsequent alkaline hydrolysis, is converted to uracil which corresponds to thymidine in its base pairing behaviour. However, 5-methylcytosine remains unmodified under these conditions. Consequently, the original DNA is converted in such a manner that methylcytosine, which originally could not be distinguished from cytosine by its hybridisation behaviour, can now be detected as the only remaining cytosine using "normal" molecular biological techniques, for example, by amplification and hybridisation or sequencing. All of these techniques are based on base pairing which can now be fully exploited. In terms of sensitivity, the prior art is defined by a method which encloses the DNA to be analysed in an agarose matrix, thus preventing the diffusion and renaturation of the DNA (bisulfite only reacts with single-stranded DNA), and which replaces all precipitation and purification steps with fast dialysis (Olek A, Oswald J, Walter J. A modified and improved method for bisulphite based cytosine methylation analysis. Nucleic Acids Res. 1996 Dec. 15;24(24):5064–6). Using this method, it is possible to analyse individual cells, which illustrates the potential of the method. However, currently only individual regions of a length of up to approximately 3000 base pairs are analysed, a global analysis of cells for thousands of possible methylation events is not possible. However, this method cannot reliably analyse very small fragments from small sample quantities either. These are lost through the matrix in spite of the diffusion protection.

An overview of the further known methods of detecting 5-methylcytosine may be gathered from the following review article: Rein, T., DePamphilis, M. L., Zorbas, H., Nucleic Acids Res. 1998, 26, 2255.

To date, barring few exceptions (e.g., Zeschnigk M, Lich C, Buiting K, Doerfler W, Horsthemke B. A single-tube PCR test for the diagnosis of Angelman and Prader-Willi syndrome based on allelic methylation differences at the SNRPN locus. Eur J Hum Genet. 1997 March–April; 5(2) :94–8) the bisulfite technique is only used in research.

Always, however, short, specific fragments of a known gene are amplified subsequent to a bisulfite treatment and either completely sequenced (Olek A, Walter J. The pre-implantation ontogeny of the H19 methylation imprint. Nat Genet. 1997 November; 17(3):275–6) or individual cytosine positions are detected by a primer extension reaction (Gonzalgo M L, Jones P A. Rapid quantitation of methylation differences at specific sites using methylation-sensitive single nucleotide primer extension (Ms-SNuPE). Nucleic Acids Res. 1997 June 15;25(12):2529–31, WO Patent 9500669) or by enzymatic digestion (Xiong Z, Laird P W. COBRA: a sensitive and quantitative DNA methylation assay. Nucleic Acids Res. 1997 June 15;25(12):2532–4). In addition, detection by hybridisation has also been described (Olek et al., WO 99 28498).

Further publications dealing with the use of the bisulfite technique for methylation detection in individual genes are: Grigg G, Clark S. Sequencing 5-methylcytosine residues in genomic DNA. Bioessays. 1994 June; 16(6):431–6, 431; Zeschnigk M, Schmitz B, Dittrich B, Buiting K, Horsthemke B, Doerfler W. Imprinted segments in the human genome: different DNA methylation patterns in the Prader-Willi/Angelman syndrome region as determined by the genomic sequencing method. Hum Mol Genet. 1997 March; 6(3): 387–95; Feil R, Charlton J, Bird A P, Walter J, Reik W. Methylation analysis on individual chromosomes: improved protocol for bisulphite genomic sequencing. Nucleic Acids Res. 1994 February 25;22(4):695–6; Martin V, Ribieras S, Song-Wang X, Rio M C, Dante R. Genomic sequencing indicates a correlation between DNA hypomethylation in the 5' region of the pS2 gene and its expression in human breast cancer cell lines. Gene. 1995 May 19;157(1–2):261–4; WO 97 46705, WO 95 15373 and WO 45560.

Fluorescence Resonance Energy Transfer (FRET)

Fluorescence resonance energy transfer (FRET) is an interaction between two molecules wherein the excited state of one molecule (the donor) transfers energy to the other molecule (the acceptor). The donor molecule is a fluorophore while the acceptor molecule may or may not be. The energy transfer occurs without the emission of photons, and is based on dipole-dipole interactions between the two molecules. Molecules that are commonly used in FRET include fluorescein, N,N,N',N'-tetramethyl-6-carboxyrhodamine (TAMRA), 6-carboxy-X-rhodamine (ROX), 4-(4'-dimethylaminophenylazo) benzoic acid (DABCYL), and 5-(2'-aminoethyl)aminonaphthalene-1-sulfonic acid (EDANS). Basic conditions for FRET include the following:

- Close proximity between the donor and acceptor molecules (typically 10–100 Å)
- The emission spectrum of the donor molecule must overlap the absorption spectrum of the acceptor molecule
- The transition dipole orientations of the donor and acceptor molecules must be approximately parallel.
- The extent of the energy transfer is dependent on the distance between the two molecules, and the overlap between the donor and acceptor spectra. It can be described by the following equation:

$$kt(r) = tD - 1 \cdot (R0/r)6$$

wherein r is the distance between the donor and the acceptor
tD is the lifetime of the donor in the absence of energy transfer
R0 is termed the Förster distance.

The efficiency of the energy transfer (for a single donor-acceptor pair) is given by:

$$E = R06/(R06 + r6)$$

Förster distances are typically in the range of 30–60 Å. Therefore FRET can be used as a highly sensitive method of measuring microscopic distances, this is particularly useful within the field of molecular biology where it has been utilised in a number of ways. It has been used in the study of protein structure, assembly, distribution, conformation and interactions, as well as the study of cell membranes and immunoassays. FRET has also been used in a number of ways in the analysis of nucleic acids. This includes the analysis of the structure and conformation of nucleic acids, hybridisation, PCR, sequencing and primer extension assays.

Another class of probe labels include fluorescence quenchers. The emission spectra of a quencher overlaps with a, fluorescent dye such that the fluorescence of the fluorescent dye is substantially diminished, or quenched, by the phenomena of fluorescence resonance energy transfer "FRET" (Clegg (1992) Meth. Enzymol., 211:353–388). A fluorescent reporter dye and quencher joined in a configuration that permits energy transfer from the fluorophore to the quencher may result in a reduction of the fluorescence of the fluorescent dye. The reporter is a luminescent compound that can be excited either by chemical reaction, producing chemiluminescence, or by light adsorption, producing fluorescence. The quencher can interact with the reporter to alter its light emission, usually resulting in the decreased emission efficiency of the reporter. The efficiency of this quenching phenomenon is directly correlated with the distance between the reporter molecule and the quencher molecule (Yaron (1979)Analytical Biochemistry, 95:228–35).

Particular quenchers include but are not limited to rhodamine dyes such as tetramethyl-6-carboxyrhodamine (TAMRA) or tetrapropano-6-carboxyrhodamine (ROX) (Bergot, U.S. Pat. No. 5,366,860).

Enzymatic Amplification

PCR is a commonly used technique that has been described, for example in U.S. Pat. Nos. 4,683,195, 4,683,202, and 4,800,159. Briefly, it is the amplification of a nucleic acid sequence by repetitive cycles of annealing and extending primer to single stranded nucleic acids followed by the denaturation of the resultant double stranded molecule. PCR, (and variations thereof) has a multitude of applications and is one of the key technologies involved in most forms of nucleic acid analysis and manipulation.

An important variation is the Multiplex-PCR, where more then 2 specific primer are used and a multitude of different specific amplificats are obtained in one reaction chamber.

There are several commonly used methods for the detection of PCR products, such as gel electrophoresis and the use of labelled primer oligonucleotides and nucleoside triphosphates. The use of fluorescent labelled nucleotides and oligomers within PCR for nucleic acid analysis is also known.

PNA FRET Probes

PNA can hybridise to its target complement in either a parallel or anti-parallel orientation. However, the anti-parallel duplex (where the carboxyl terminus of PNA is aligned with the 5' terminus of DNA, and the amino terminus is aligned with the 3'-terminus of DNA) is typically more stable (Egholm (1993) Nature, 365:566–68). PNA probes are known to bind to target DNA sequences with high specificity and affinity (Coull, U.S. Pat. No. 6,110,676). The PNA FRET probe examples of the present invention, with reporter or quencher moieties, are designed such that the PNA anneals in the anti-parallel orientation with the target sequences.

PNA may be synthesized at any scale on automated synthesizers. The PNA FRET probes may be synthesized on many of the commonly used solid supports. After synthesis is complete, the PNA may be cleaved from the support, purified, analysed and quantitated. Fluorescent-labeled PNA probes have demonstrated desirable properties in hybridization assays (Hyldig-Nielsen, U.S. Pat. No. 5,985,563).

Genomic DNA for further amplification is obtained from DNA of cells, tissue or other test samples using standard methods. This standard methodology is found in references such as Fritsch and Maniatis eds., Molecular Cloning: A Laboratory Manual, 1989.

Real Time PCR

Real time PCR monitoring using fluorescence has been described in several manners. Firstly, the binding of double stranded DNA specific fluorescent dyes such as ethidium bromide allows for the monitoring of the accumulation of PCR product by correlation with increased fluorescence. A second detection method, polymerase mediated exonuclease cleavage utilises the 5' exonuclease activity of polymerases such as Taq. An oligonucleotide probe that is complementary to the PCR product, yet distinct from the PCR primer is labelled with a FRET pair such that the donor molecule is quenched by an acceptor molecule. During PCR amplification, the 5' exonuclease proceeds to digest the probe, separating the FRET pair and leading to increased fluorescence. A variation on this technology uses a nucleic acid wherein the FRET pair is internally quenched, for example, by having a hairpin conformation. Upon hybridisation to a sequence of interest, the FRET pair is separated and the donor molecule emits fluorescence. This technology can be used, for example for the analysis of SNPs.

An alternative technology is based on the use of two species of hybridisation probes, each labelled with a member of a FRET pair. Upon hybridisation of both probes to the target sequence in adequate proximity, a fluorescent signal is emitted. Again, this technology may be used for the detection of SNPs.

A major advantage of the use of such FRET based PCR technologies is that the reaction may be monitored in a closed tube reaction, suitable for use in high and medium throughput and reducing the probability of contamination.

DESCRIPTION OF THE INVENTION

According to the present invention there is provided a method for the cytosine methylation detection in a DNA sample, comprising the following steps:
a) a genomic DNA sample is treated in a manner capable of distinguishing methylated from unmethylated cytosine bases;
b) the pre-treated DNA is amplified using at least one oligonucleotide primer, a polymerase and a set of nucleotides of which at least one is marked with a first type of label;
c) a sequence-specific oligonucleotide or oligomer probe is hybridized to the amplification product and a FRET occurs if the oligonucleotide or oligomer probe, marked with a second type of label, binds in close proximity to one of the labeled nucleotides that was incorporated into the amplification product;
d) the level of methylation of the sample is determined by the level of interaction between said first and second type of label.

According to the invention it is preferred that the first type of label is a donor fluorophore and the second type of label is an acceptor fluorophore and that the extent of fluorescence resonance energy transfer (FRET) is measured. It is further preferred that the first type of label is an acceptor fluorophore and the second type of label is a donor fluorophore and that the extent of fluorescence resonance energy transfer (FRET) is measured.

A further preferred embodiment of the present invention is characterised in that the nucleotides of step b) contain a fluorescent moiety and the probe in step c) a quencher moiety. It is also preferred according to the invention that the nucleotides of step b) contain a quencher moiety and the probe in step c) a fluorescent moiety.

According to the invention it is also preferred that the polymerase has no 5' to 3' exonuclease activity in order to prevent degradation of the probe.

It is further preferred according to the invention that a change in fluorescence intensity is monitored in real-time during the amplification reaction.

It is also especially preferred according to the present invention that a change in fluorescence intensity is monitored at end-point of target amplification.

According to another preferred embodiment of the present invention the amplification reaction is achieved with the polymerase chain reaction (PCR).

According to the invention it is preferred that the probe contains only one CpG or that the probe contains several CpGs. Especially in this case it is further preferred that each probe for each CpG has a fluorescent label.

In a further preferred embodiment of the present invention the probe can be end labeled or internally labeled.

It is also preferred according to the invention that the methylation information is determined by the change in fluorescence intensity during subsequent rounds or cycles of PCR.

It is also preferred that the sample DNA is only amplified by chosen PCR primers if a certain methylation state is present at a specific site in the sample DNA.

According to the present invention a method is preferred wherein the sample DNA is only amplified if a certain methylation state was present at a specific site in the sample DNA, the sequence context of which is essentially complementary to one or more oligonucleotides or PNA oligomers which are additionally used in the PCR reaction.

It is also preferred that the amplification from the 3'-end of the probe is blocked by phosphorylation.

According to the invention it is also preferred that a melting curve is generated at the end of the PCR to gather additional data.

It is especially preferred within the scope of the present invention that the fluorescent moiety is a fluorescein dye, a rhodamine dye, or a cyanine dye. Especially preferred is also that the quencher moiety is a rhodamine dye.

It is an especially preferred feature of the present invention that the deamination treatment of the DNA is performed with a bisulfite reagent.

It is also preferred according to the invention that the DNA sample is cleaved prior to deamination treatment with restriction endonucleases.

In a preferred embodiment of the method of the invention the DNA sample is isolated from mammalian sources e.g. cell lines, blood, sputum, faeces, urine, cerebrospinal fluid, tissue embedded in paraffin, for example, ocular tissue, intestine, kidney, brain, heart, prostate, lung, chest or liver, histological slides and all possible combinations.

It is another preferred embodiment of the present invention to use of a pre-treated genomic DNA within the method according to the present invention for the determination of the methylation status of a corresponding genomic DNA.

Another object of the present invention is to provide a diagnostic kit for the detection of the methylation of cytosine bases in genomic DNA samples, comprising reagents for the selective deamination of cytosine bases in genomic DNA, one or more primers and labeled nucleotides for the amplification step, a detectable probe and optionally protocols or instructions for one of the methods according to one of the preceding claims.

The invention describes a method to determine the presence of specific CpG dinucleotides in a fragment of DNA using fluorescence resonance energy transfer (FRET). This can be used to obtain information about sequence properties of a sample DNA fragment. For example, a point mutation could be identified in a fragment if a nucleotide is present in its sequence as a result of this mutation which is not present in the wild type.

The method is preferably used to measure cytosine methylation. As mentioned above, bisulphite leads to the selective deamination of cytosine, leaving 5-methylcytosine essentially unchanged. Methylation of cytosine occurs almost exclusively in the sequence context 5'-CG-3'. Therefore, after bisulphite treatment, certain dinucleotides containing C do not occur anymore in one strand, but they may still occur in the complementary strand formed in the amplification of bisulphite treated DNA, for example using the polymerase chain reaction (PCR).

This invention provides a method for visualizing the methylation status of a CpG at defined positions in a very sensitive way with very low background signal.

The method briefly comprises the following steps of
a) treating a genomic DNA sample in a manner capable of distinguishing methylated from unmethylated cytosine bases;
b) amplifying the pre-treated DNA using at least one oligonucleotide primer, a polymerase and a set of nucleotides of which at least one is marked with a first type of label;
c) hybridising a sequence-specific oligonucleotide or oligomer probe to the amplification product, a FRET occurs if the oligonucleotide or oligomer probe, marked with a second type of label, binds in close proximity to one of the labeled nucleotides that was incorporated into the amplification product;
d) determining the level of methylation of the sample by measuring by the level of interaction between said first and second type of label.

In a preferred embodiment of the invention, the first type of label is a donor fluorophore and the second type of label is an acceptor fluorophore and that the extent of fluorescence resonance energy transfer (FRET) is measured.

In a further preferred embodiment of the invention, said first type of label is an acceptor fluorophore and the second type of label is a donor fluorophore and that the extent of fluorescence resonance energy transfer (FRET) is measured.

It is preferred that two or more CpGs are separately interrogated in an amplification reaction.

Preferably, separate probes for each CpG are used, each with its own fluorescent label.

The instant invention also enables a multiplex PCR to rapidly determine optimal assay parameters and a fast, cost-effective, and accurate system for the quantitative analysis of target analytes. A multiplexed assay can for example be designed in a standard 96 well microtiter plate format at room temperature using conventional robotic systems for sample delivery and preparation.

Preferably, the oligonucleotide or oligomer probes used comprise one or more nucleotide analogs selected from a nucleobase analog, a 2'-deoxyribose analog, an internucleotide analog, PNA or LNA.

Although the detection of C or G nucleotides (in the complementary strand) after bisulphite treatment in the context CpG is the preferred application, also any other nucleotide or polymorphism can in principle be detected. The preferred application is to determine the methylation status of certain CpG positions by determining the level of interaction between an unconverted C in the bisulphite treated DNA and a labeled oligonucleotide hybridised thereto. Accordingly, Guanin in the complementary strand (after PCR) can be used for the same purpose.

Also, converted positions after bisulphite treatment can be identified by detecting thymine (or adenine in the complementary strand) at selected positions using this technology. However, design of probes becomes more difficult as it is not possible to distinguish between T that was in the original genomic sequence and T positions that were created through bisulphite conversion, indicating lack of methylation at the respective cytosines.

In more detail, this method for the detection of specific nucleotides in a DNA sample is characterized in that an isolated genomic DNA sample is treated in a manner capable of distinguishing methylated from unmethylated cytosine bases and the pre-treated DNA is amplified using at least one oligonucleotide primer, a polymerase and a set of nucleotides at least one of which is marked with a first type of label, in a first embodiment a donor fluorophore and in a second embodiment an acceptor fluorophore.

Preferably, the acceptor and donor dyes (fluorophores) are chosen in a way that the emission wavelength of the donor dye overlaps with the excitation wavelength of the acceptor dye. It is preferred that the emission and excitation spectra are sharp peaks and that the emission spectra of the dyes are unlikely to overlap.

It is preferred that the polymerase has no 5' to 3' exonuclease activity to prevent degradation of the probe.

For example, dGTP is labeled with a fluorescent dye. The labeled dGTP is incorporated only where there was a methylated cytosine in the original DNA sample. Alternatively, the dCTP can be labeled with a fluorescent dye.

After the extension phase, the DNA is denatured and then allowed to reanneal.

A sequence-specific oligonucleotide or oligomer probe (referred to as oligomer probes if DNA analogs like PNA are used), marked with a second type of label that is in a first embodiment an acceptor fluorophore and in a second embodiment a donor fluorophore hybridizes to the amplification product. Preferably, amplification from the 3' end of the probe is blocked by phosphorylation (with didesoxynucleotides).

The labels are preferably introduced into the oligonucleotide probes by standard enzymatic methods, such as the use of 5' labeled amplification primers for 5' labeling or fluorescent-labeled base analogs for internal labeling.

A FRET reaction occurs if the fluorescently labeled oligonucleotide, preferably in one embodiment a fluorescent moiety binds in close proximity to a nucleotide labeled with a quencher moiety, that was incorporated into the amplification product or in another embodiment a quencher moiety that binds in close proximity to a nucleotide labeled with a fluorescent moiety that was incorporated into the amplification product (FIG. 1).

It is preferred that the probe is positioned in several places relative to the CpG. The conformation of the DNA controls the spacing of the two fluorescent dyes. Preferently, the positioning is optimized for each CpG.

In a preferred embodiment, the probe is separated from the amplification primers or alternatively it is attached to the 5' end of one of the primers.

This way, the level of methylation can be determined, identifying the CG dinucleotides. If a TG dinucleotide is present instead, no FRET will be observed. Therefore, this method can be directly used to monitor DNA methylation (FIG. 2).

In a preferred embodiment of the invention a real time monitoring of the FRET signal is performed during the amplification reaction. This way, the progress of the amplification can be examined (FIG. 3). Very preferably the amplification reaction is a polymerase chain reaction (PCR), even though other amplification procedures for example cloning or SDA (Strand Displacement Amplification) are also preferred.

In another preferred embodiment of the invention the change in fluorescence intensity is monitored at end-point of target amplification. End-point analysis of the PCR entails fluorescent dye signal measurement when thermal cycling and amplification is complete. Results are reported in terms of the change in fluorescence, i.e. fluorescence intensity units, of the fluorescent dye signal from start to finish of the PCR thermal cycling, preferably minus any internal control signals.

It is also preferred that a melting curve is generated at the end of the PCR to gather additional data.

In another preferred embodiment of the invention the CpG dinucleotide occurs only once in the amplification product. As outlined above, this is very helpful if the presence of the FRET signal is directly used to draw conclusions about the sequence characteristics of the sample DNA.

For example, if only one labeled CG is present in an amplification product of a bisulphite treated sample and a fluorescently labeled probe binds in close proximity to it, a FRET occurs and direct conclusions can be drawn that a methylated cytosine was present in a certain position in the genomic DNA sample.

If several labeled CGs are present for example in an amplification product of a bisulphite treated sample and probes bind in close proximity to them, each with its own fluorescent label, several FRET reactions occur and conclusions can be drawn about the methylated cytosines from all sites involved.

In a further preferred embodiment of the invention the methylation information is determined by the change in fluorescence intensity during subsequent rounds of PCR.

Preferably, the sample is illuminated during the amplification reaction with light of appropriate wavelength.

In a preferred embodiment of the invention, prior to the PCR either essentially all cytosines in the DNA sample are selectively deaminated, but 5-methylcytosines remain essentially unchanged or essentially all 5-methylcytosines in the DNA sample are selectively deaminated, but cytosines remain essentially unchanged. Cytosine-guanine (CpG) dinucleotides are detected, allowing conclusions about the methylation state of cytosines in said CpG dinucleotides in said DNA sample. This deamination is preferably performed using a bisulphite reagent.

Preferably, the sample DNA is only amplified by chosen PCR primers if a certain methylation state is present at a specific site in the sample DNA the sequence context of which is essentially complementary to one or more of said chosen PCR primers. This can be done using primers annealing selectively to bisulphite treated DNA which contains in a certain position either a TG or a CG, depending on the methylation status in the genomic DNA. Primers can be designed for both cases. A primer could contain a G at its 3'-end, therefore if would only bind to a DNA containing a C at the respective position and therefore this primer will only or preferentially amplify methylated DNA because the C is indicative of a methylation in this position after bisulphite treatment. This method is known as MSP, methylation sensitive PCR.

In another preferred embodiment of the invention, the sample DNA is only amplified if a certain methylation state is present at a specific site in the sample DNA the sequence context of which is essentially complementary to one or more oligonucleotides or PNA oligomers which are additionally used in the PCR reaction. These oligonucleotides or PNA oligomers bind selectively to the template DNA and prevent its amplification depending on the methylation state of the DNA prior to bisulphite conversion.

Preferably, the fluorescent moiety is a fluorescein dye, a rhodamine dye, or a cyanine dye and the quencher moiety a rhodamine dye.

In another preferred variant of the invention the DNA sample is cleaved prior to deamination (for example bisulphite) treatment with restriction endonucleases.

Preferred is also a method whereby the enzymatic amplification of the treated DNA is such that only one strand of the DNA sample is amplified.

Preferably, the DNA sample is isolated from mammalian sources e.g. cell lines, blood, sputum, faeces, urine, cerebrospinal fluid, tissue embedded in paraffin, for example, ocular tissue, intestine, kidney, brain, heart, prostate, lung, chest or liver, histological slides and all possible combinations.

Another embodiment of the present invention is a diagnostic kit for the detection of the methylation of cytosine bases in genomic DNA samples, comprising reagents for the selective deamination of cytosine bases in genomic DNA, one or more primers and fluorescently labeled nucleotides for the amplification step and optionally protocols or instructions for one of the methods according to one of the preceding claims.

This kit can also comprise several additional items for example detectable probes.

The components of said kit, as an example, could comprise receptacles for the following in sufficient quantities to carry out the method:
1) Reagents for the bisulfite conversion of sample DNA.
2) Reagents for the amplification of the converted sample and incorporation of fluorophore labelled nucleotides including:
   a) nucleic acid primer and
   b) appropriate mix of nonlabeled and fluorophore labeled nucleotides and
   c) DNA polymerase able to incorporate the fluorophore labelled nucleotides
3) Instructions for use The term 'instructions for use' should cover a tangible expression describing the reagent concentrations for the assay method, parameters such as the relative amounts of reagents to be combined, maintenance times for reagents/sample mixtures, temperature, buffer conditions and the like.

In the following, steps of preferred embodiments of the invention are described in more detail.

DNA Isolation

The genomic DNA sample must be isolated from tissue or cellular sources. For mammals, more preferably humans, the DNA sample may be taken from any tissue suspected of expressing the target site within the genome and also from, such as cell lines, blood, sputum, faeces, urine, cerebrospinal fluid, tissue embedded in paraffin; for example, tissue of intestine, kidney, brain, heart, prostate, lung, chest or liver, histological slides, but not limited to those. Extraction may be by means that are standard to one skilled in the art, these include the use of detergent lysates, sonification and vortexing with glass beads. Once the nucleic acids have been extracted the genomic double stranded DNA is used for analysis.

Bisulfite Treatment

The sample DNA is then treated chemically in order to convert the unmethylated cytosine bases into uracil. The chemical modification may be by means of, for example, (but not limited to) a bisulfite solution. Said chemical conversion may take place in any format standard in the the art. This includes but is not limited to modification within agarose gel or in denaturing solvents.

Wherein the chemical modification takes the form of a bisulfite treatment of the DNA the following steps may be followed.

The double stranded DNA must be denatured. This may take the form of a heat denaturation carried out at variable temperatures. For high molecular weight DNA, the denaturation temperature is generally greater than 90° C. However, the analysis may be upon smaller fragments which do not require such high temperatures. In addition as the reaction proceeds and the cytosine residues are converted to uracil the complementarity between the strands decreases. Therefore, a cyclic reaction protocol may consist of variable denaturation temperatures.

The bisulfite conversion then consists of two important steps, the sulfonation of the cytosine and the subsequent deamination. The equilibra of the reaction are on the correct side at two different temperatures for each stage of the reaction. Taking into account the kinetics of the reactions it is preferable that the reaction takes place under cyclic conditions, with changing temperatures. The temperatures and length at which each stage is carried out may be varied according to the specific requirement of the situation. However, a preferred variant of the method comprises a change of temperature from 4 C (10 minutes) to 50 C (20 minutes). This form of bisulfite treatment is state of the art with reference to WO 99/28498.

Said chemical conversion may take place in any format standard in the art. This includes but is not limited to modification within agarose gel, in denaturing solvents or within capillaries.

Bisulfite conversion within agarose gel is state of the art and has been described by Olek et al, Nucl. Acids. Res. 1996, 24, 5064–5066. The DNA fragment is embedded in agarose gel and the conversion of cytosine to uracil takes place with hydrogensulfite and a radical scavenger. The DNA may then be amplified without need for further purification steps.

In a further preferred embodiment the DNA conversion may take place without an agarose matrix. The DNA may incubated at increased temperatures with hydrogensulfite and a radical scavenger. Said reaction takes place within an organic denaturing solvent. Examples of denaturing solvents include, but are not limited to, Polyethylene glycol dialkyl polyethylenglycol-dialkylether, dioxane and substituted derivatives, urea or derivatives, acetonitrile, primary alcohols, secondary alcohols, tertiary alcohols, DMSO or THF.

In a further embodiment, prior to chemical treatment the DNA sample is transferred into a heatable capillary that is permeable to small molecules. The reaction steps of the chemical modification may then be carried out in the capillary tubes by means of the addition and removal of reagents through connected capillaries.

Subsequent to the chemical treatment the two strands of the DNA may no longer be complementary.

Amplification and Incorporation of labeled Nucleotides

Fractions of the so treated genomic DNA are then enzymatically amplified using oligonucleotide primers. The length and design of said primers may be specific to the area of the genome to be analysed. As such a wide range of primers are suitable for use in this technique. Such primer design is within the state of the art.

An appropriate fraction of the nucleotides presented in the amplification reaction, for example the G nucleotides, are labeled with either a first or second type of label, the first type being a fluorophore and the second type a quencher or vice versa. Acceptable fluorophores for labeling the nucleotides are well known to those skilled in the art and include, but are not limited to, fluorescein, rhodamine, cyanine, phycoerythrin, Cy 5, Cy 5.5, Cy 7, LC Red 640 or LC Red 705 whereas the acceptable quenchers are rhodamine dyes. Attaching those dyes to the nucleotides lies within the state of the art.

In a preferred embodiment of this invention the sample is illuminated during the amplification reaction with light of appropriate wavelength.

The skill of the invention lies in the interpretation of a FRET signal during states, where a sequence-specific oligonucleotide probe is hybridized to an amplification product and a FRET occurs if the fluorescently labeled oligonucleotide binds in close proximity to one of the labeled nucleotides that were incorporated into the amplification product in order to gain knowledge of the methylation state of the sample.

Advanced Data Processing

It is anticipated that the method will be used for the high throughput analysis of genomic DNA samples. Therefore, the invention also involves analysis of data using a computing device. In a preferred embodiment said device may comprise one or more databases. In a further preferred embodiment said device may comprise one or more learning algorithms.

Legend:
1: Bisulfite Treatment
2: Incorporation of labeled nucleotide
3: Detection of target by Fret
4: Real-Time PCR DNA extracted from a tissue is treated with sodium bisulfite (A). Into the bisulfite treated DNA (single strand (B) dGTPs are incorporated (C+D) that are labeled with a fluorescent dye during a real-time PCR. A FRET occurs if the fluorescently labeled oligonucleotide binds in close proximity to one of the labeled nucleotides that was incorporated into the amplification product (E).

FIG. 2

Legend:
1. Bisulfite treatment
2. PCR with labeled dGTP
3. Extension of primer
4. Denaturation
5. Annealing and fluorescence monitoring
6. More Cycles In the first step DNA of interest (SEQ ID NO:1) is chemically treated to yield the sequence shown in the second row (SEQ ID NO:2), wherein the only cytosines remaining in the sequence are those that were methylated in the original sample. PCR primers (shown in the third row. SEQ ID NO:3) designed to target one of the DNA strands anneal to the template (SEQ ID NO:2) and extend it by incorporating labeled nucleotides (dGTP) to yield SEQ ID NO:4. The labeled dGTP is incorporated only where there was a methylated cytosine in the original DNA sample. After the extension phase, the DNA (SEQ ID NO:2, sixth row) is denatured, allowed to reanneal with primers (SEQ ID NO:5, left, and SEQ ID NO:6, right) and the fluorescence monitored. With each round of PCR, more targets complementary to the probe accumulate. The amount of fluorescence emitted from the probe is measured.

Figure 1:
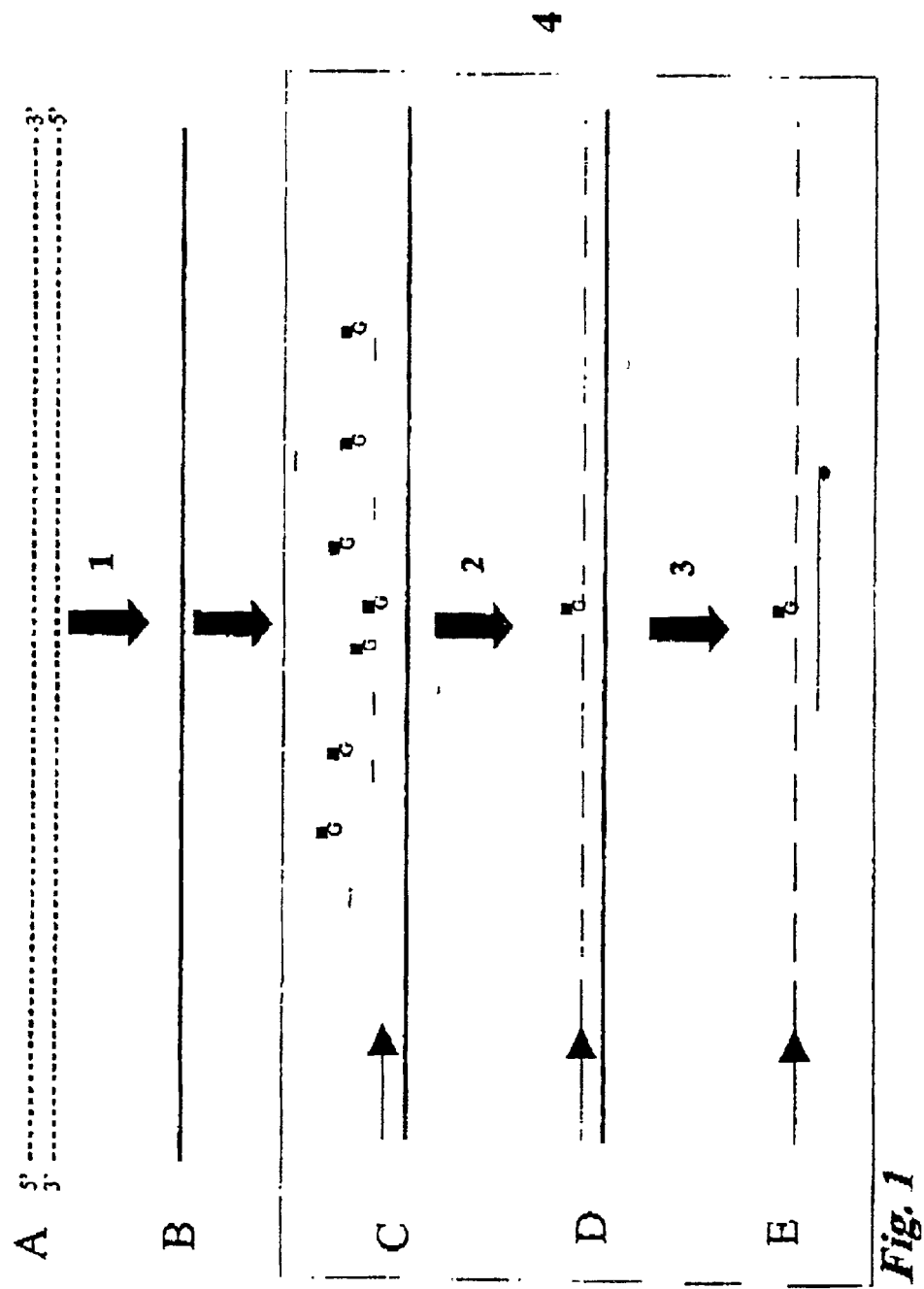
FIG. 1
Figure 2:
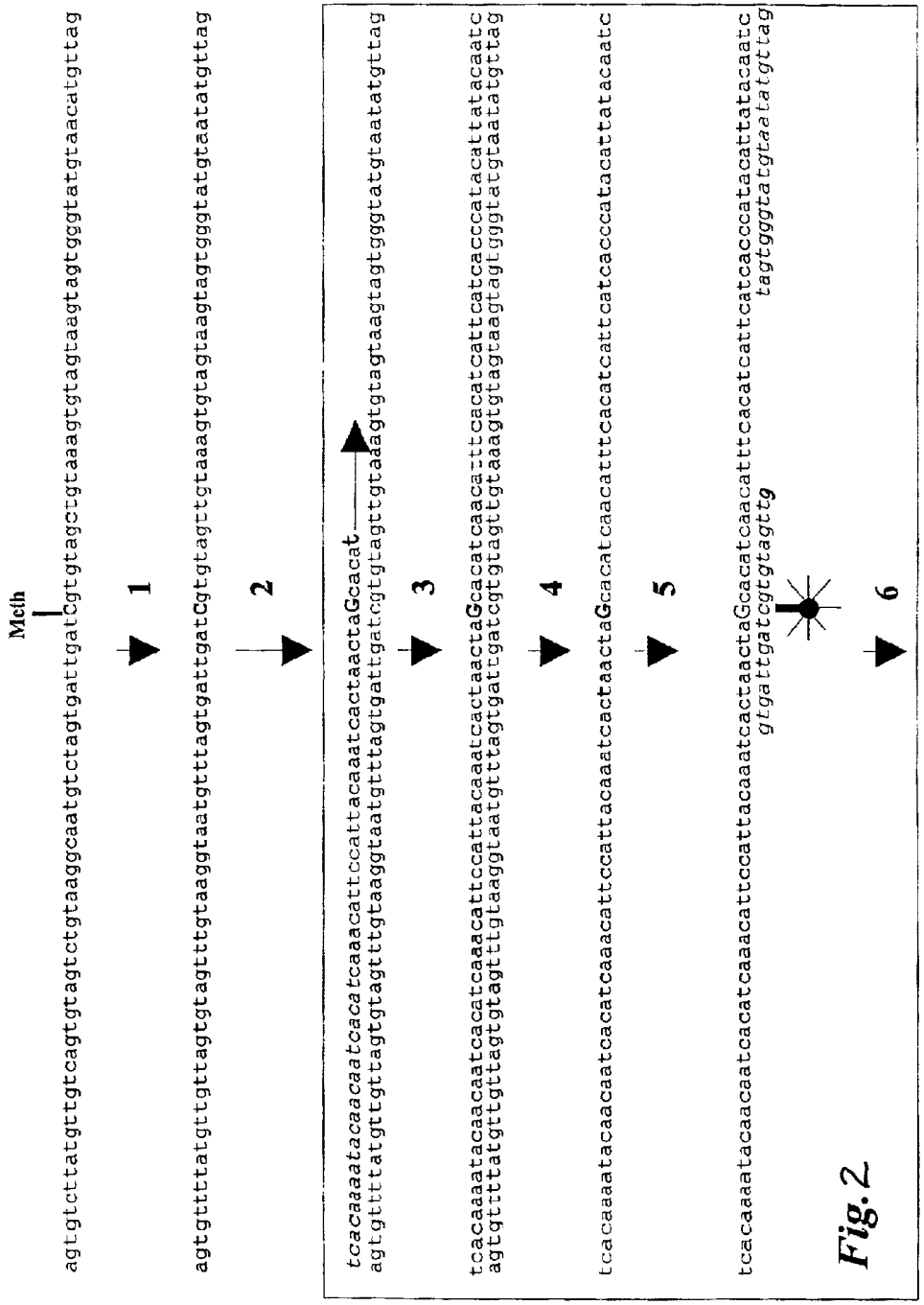
Figure 3:
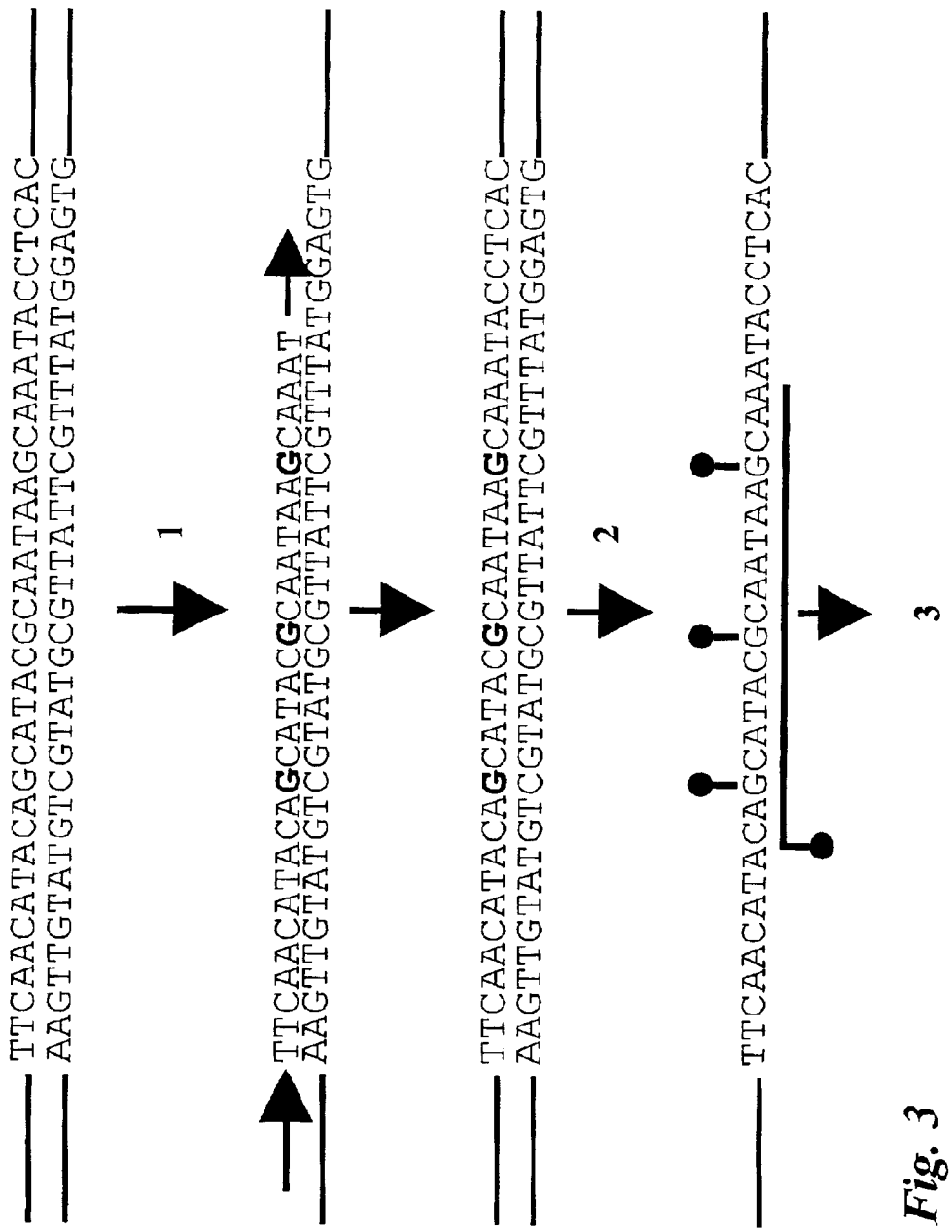

FIG. 3
Legend:
1. PCR with unlabeled dCTP, dATP, dTTP and labeled dGTP
2. Hybridization of fluorescent-labeled gene specific oligonucleotide 3. FRET, real-time fluorescence detection A PCR is performed with primers that target one of the DNA strands (SEQ ID NO:7, first row, and SEQ ID NO:8, second row). The first primer (SEQ ID NO:9, third row) anneals to the template (SEQ ID NO:8, fourth row) and extends it by incorporating the appropriate nucleotides. One of the nucleotides, in this case dGTP, is labeled with a fluorescent dye. A sequence-specific oligonucleotide probe hybridizes to the site of interest of SEQ ID NO:9 to afford SEQ ID NO:10, fifth row. If the labeled guanine is present (SEQ ID NO:10, last row), a FRET reaction occurs. The energy emitted from the guanine is transferred to the label on the probe. The energy emitted from the probe is detected by real-time fluorescence detection.

What is claimed is:

1. A method for the cytosine methylation detection in a DNA sample, comprising the following steps:
   a) a genomic DNA sample is treated in a manner capable of distinguishing methylated from unmethylated cytosine bases;
   b) the pre-treated DNA is amplified using at least one oligonucleotide primer, a polymerase and a set of nucleotides of which at least one is marked with a first type of label;
   c) a sequence-specific oligonucleotide or oligomer probe is hybridized to the amplification product and a fluorescence resonance energy transfer (FRET) occurs if the oligonucleotide or oligomer probe, marked with a second type of label, binds in close proximity to one of the labeled nucleotides that was incorporated into the amplification product;
   d) the level of methylation of the sample is determined by the level of interaction between said first and second type of label.

2. A method according to claim 1, characterised in that the first type of label is a donor fluorophore and the second type of label is an acceptor fluorophore and that the extent of fluorescence resonance energy transfer (FRET) is measured.

3. A method according to claim 1, characterised in that the first type of label is an acceptor fluorophore and the second type of label is a donor fluorophore and that the extent of fluorescence resonance energy transfer (FRET) is measured.

4. A method according to claim 1, characterised in that the nucleotides of step b) contain a fluorescent moiety and the probe in step c) a quencher moiety.

5. A method according to claim 1, characterised in that the nucleotides of step b) contain a quencher moiety and the probe in step c) a fluorescent moiety.

6. A method according to claim 1, characterised in that the polymerase has no 5' to 3' exonuclease activity in order to prevent degradation of the probe.

7. A method according to claim 1, characterized in that a change in fluorescence intensity is monitored in real-time during the amplification reaction.

8. A method according to claim 1, characterized in that a change in fluorescence intensity is monitored at end-point of target amplification.

9. A method according to claim 1, characterized in that the amplification reaction is achieved with the polymerase chain reaction (PCR).

10. A method according to claim 1, characterized in that the probe contains only one CpG.

11. A method according to claim 1, characterized in that the probe contains several CpGs.

12. A method according to claim 11, characterized in that each probe for each CpG has a fluorescent label.

13. A method according to claim 1, characterized in that the probe can be end labeled or internally labeled.

14. A method according to claim 1, characterized in that the methylation information is determined by the change in fluorescence intensity during subsequent rounds of PCR.

15. A method according to claim 1, characterized in that the sample DNA is only amplified by chosen PCR primers if a certain methylation state is present at a specific site in the sample DNA.

16. A method according to claim 1, characterized in that the sample DNA is only amplified if a certain methylation state was present at a specific site in the sample DNA, the sequence context of which is essentially complementary to one or more oligonucleotides or PNA oligomers which are additionally used in the PCR reaction.

17. A method according to claim 1, characterized in that the amplification from the 3'-end of the probe is blocked by phosphorylation.

18. A method according to claim 1 characterized in that a melting curve is generated at the end of the PCR to gather additional data.

19. A method according to claim 1 wherein the fluorescent moiety is a fluorescein dye, a rhodamine dye, or a cyanine dye.

20. A method according to claim 1 wherein the quencher moiety is a rhodamine dye.

21. A method according to claim 1 wherein the deamination treatment of the DNA is performed with a bisulfite reagent.

22. A method according to claim 1 wherein the DNA sample is cleaved prior to deamination treatment with restriction endonucleases.

23. A method according to claim 1 wherein the DNA sample is isolated from mammalian sources.

24. The method as claimed in claim 23 wherein the DNA sample is isolated from a source selected from the group consisting of cell lines, blood, sputum, faeces, urine, cerebrospinal fluid, tissue embedded in paraffin, for example, ocular tissue, intestine, kidney, brain, heart, prostate, lung, chest or liver, histological slides and all possible combinations.

* * * * *

SEQUENCE LISTING

<160> NUMBER OF SEQ ID NOS: 10

<210> SEQ ID NO 1
<211> LENGTH: 96
<212> TYPE: DNA
<213> ORGANISM: Artificial Sequence
<220> FEATURE:
<223> OTHER INFORMATION: example for DNA sample
<220> FEATURE:
<221> NAME/KEY: modified_base
<222> LOCATION: (51)..(51)
<223> OTHER INFORMATION: methylated cytosine

<400> SEQUENCE: 1
agtgtcttat gttgtcagtg tagtctgtaa ggcaatgtct agtgattgat cgtgtagctg     60
taaagtgtag taagtagtgg gtatgtaaca tgttag                              96

<210> SEQ ID NO 2
<211> LENGTH: 96
<212> TYPE: DNA
<213> ORGANISM: Artificial Sequence
<220> FEATURE:
<223> OTHER INFORMATION: chemically treated DNA sample

<400> SEQUENCE: 2
agtgttttat gttgttagtg tagtttgtaa ggtaatgttt agtgattgat cgtgtagttg     60
taaagtgtag taagtagtgg gtatgtaata tgttag                              96

<210> SEQ ID NO 3
<211> LENGTH: 56
<212> TYPE: DNA
<213> ORGANISM: Artificial Sequence
<220> FEATURE:
<223> OTHER INFORMATION: labeled primer
<220> FEATURE:
<221> NAME/KEY: modified_base
<222> LOCATION: (51)..(51)
<223> OTHER INFORMATION: fluorescently labeled primer
<220> FEATURE:
<221> NAME/KEY: modified_base
<222> LOCATION: (51)..(51)
<223> OTHER INFORMATION: fluorescently labeled guanine

<400> SEQUENCE: 3
tcacaaaata caacaatcac atcaaacatt ccattacaaa tcactaacta gcacat          56

<210> SEQ ID NO 4
<211> LENGTH: 96
<212> TYPE: DNA

```
<213> ORGANISM: Artificial Sequence
<220> FEATURE:
<223> OTHER INFORMATION: labeled oligonucleotide
<220> FEATURE:
<221> NAME/KEY: modified_base
<222> LOCATION: (51)..(51)
<223> OTHER INFORMATION: fluorescently labeled guanine

<400> SEQUENCE: 4
tcacaaaata caacaatcac atcaaacatt ccattacaaa tcactaacta gcacatcaac    60
atttcacatc attcatcacc catacattat acaatc                              96

<210> SEQ ID NO 5
<211> LENGTH: 19
<212> TYPE: DNA
<213> ORGANISM: Artificial Sequence
<220> FEATURE:
<223> OTHER INFORMATION: primer oligonucleotide

<400> SEQUENCE: 5
gtgattgatc gtgtagttg                                                 19

<210> SEQ ID NO 6
<211> LENGTH: 22
<212> TYPE: DNA
<213> ORGANISM: Artificial Sequence
<220> FEATURE:
<223> OTHER INFORMATION: primer oligonucleotide

<400> SEQUENCE: 6
tagtgggtat gtaatatgtt ag                                             22

<210> SEQ ID NO 7
<211> LENGTH: 37
<212> TYPE: DNA
<213> ORGANISM: Artificial Sequence
<220> FEATURE:
<223> OTHER INFORMATION: example for DNA sample

<400> SEQUENCE: 7
ttcaacatac agcatacgca ataagcaaat acctcac                             37

<210> SEQ ID NO 8
<211> LENGTH: 37
<212> TYPE: DNA
<213> ORGANISM: Artificial Sequence
<220> FEATURE:
<223> OTHER INFORMATION: example for DNA sample

<400> SEQUENCE: 8
aagttgtatg tcgtatgcgt tattcgttta tggagtg                             37

<210> SEQ ID NO 9
<211> LENGTH: 30
<212> TYPE: DNA
<213> ORGANISM: Artificial Sequence
<220> FEATURE:
<223> OTHER INFORMATION: labeled primer
<220> FEATURE:
<221> NAME/KEY: modified_base
<222> LOCATION: (12)..(12)
<223> OTHER INFORMATION: fluorescently labeled guanine
<220> FEATURE:
<221> NAME/KEY: modified_base
<222> LOCATION: (18)..(18)
<223> OTHER INFORMATION: fluorescently labeled guanine
<220> FEATURE:
<221> NAME/KEY: modified_base
```

-continued

```
<222> LOCATION: (25)..(25)
<223> OTHER INFORMATION: fluorescently labeled guanine

<400> SEQUENCE: 9
ttcaacatac agcatacgca ataagcaaat                                          30

<210> SEQ ID NO 10
<211> LENGTH: 37
<212> TYPE: DNA
<213> ORGANISM: Artificial Sequence
<220> FEATURE:
<223> OTHER INFORMATION: labeled DNA sample
<220> FEATURE:
<221> NAME/KEY: modified_base
<222> LOCATION: (12)..(12)
<223> OTHER INFORMATION: fluorescently labeled guanine
<220> FEATURE:
<221> NAME/KEY: modified_base
<222> LOCATION: (18)..(18)
<223> OTHER INFORMATION: fluorescently labeled guanine
<220> FEATURE:
<221> NAME/KEY: modified_base
<222> LOCATION: (25)..(25)
<223> OTHER INFORMATION: fluorescently labeled guanine

<400> SEQUENCE: 10
ttcaacatac agcatacgca ataagcaaat acctcac                                  37
```